United States Patent
Ungaro et al.

(10) Patent No.: US 9,370,089 B2
(45) Date of Patent: Jun. 14, 2016

(54) SELF-SHIELDED VERTICAL PROTON-LINEAR ACCELERATOR FOR PROTON-THERAPY

(71) Applicant: ADAM S.A., Geneva (CH)

(72) Inventors: Donatella Ungaro, Gex (FR); Jacopo Nardulli, Thoiry (FR)

(73) Assignee: ADAM S.A., Geneva (CH)

( * ) Notice: Subject to any disclaimer, the term of this patent is extended or adjusted under 35 U.S.C. 154(b) by 0 days.

(21) Appl. No.: 14/321,079

(22) Filed: Jul. 1, 2014

(65) Prior Publication Data

US 2015/0015167 A1 Jan. 15, 2015

(30) Foreign Application Priority Data

Jul. 10, 2013 (EP) .................................. 13175973

(51) Int. Cl.
*H05H 9/00* (2006.01)
*H05H 7/22* (2006.01)
*H05H 9/04* (2006.01)

(52) U.S. Cl.
CPC . *H05H 9/00* (2013.01); *H05H 7/22* (2013.01); *H05H 9/041* (2013.01)

(58) Field of Classification Search
USPC .................................................. 315/500–505
See application file for complete search history.

(56) References Cited

U.S. PATENT DOCUMENTS

| | | | |
|---|---|---|---|
| 3,287,672 A | 11/1966 | Heinz | |
| 4,392,080 A | 7/1983 | Maschke | |
| 5,014,014 A | 5/1991 | Swenson | |
| 7,026,636 B2 * | 4/2006 | Yanagisawa | A61N 5/1042 250/492.3 |
| 7,554,275 B2 * | 6/2009 | Amaldi | H05H 6/00 250/492.3 |
| 7,609,009 B2 * | 10/2009 | Tanaka | H05H 9/00 250/396 R |
| 8,368,043 B2 * | 2/2013 | Havelange | A61N 5/1081 250/454.11 |
| 8,405,056 B2 * | 3/2013 | Amaldi | 250/396 R |
| 8,575,563 B2 * | 11/2013 | Cameron | A61N 5/10 250/396 ML |
| 8,791,656 B1 * | 7/2014 | Zwart | H05H 7/04 315/500 |
| 2009/0224700 A1 * | 9/2009 | Chen | H05H 9/00 315/505 |
| 2010/0060209 A1 * | 3/2010 | Balakin | H05H 13/04 315/505 |
| 2012/0126727 A1 * | 5/2012 | Hamm | H05H 9/045 315/505 |
| 2012/0181456 A1 * | 7/2012 | Chen | G21K 1/087 250/492.3 |

OTHER PUBLICATIONS

European Search Report for corresponding European Patent Application No. 13175973.0 mailed Dec. 4, 2013.

\* cited by examiner

*Primary Examiner* — Douglas W Owens
*Assistant Examiner* — Srinivas Sathiraju
(74) *Attorney, Agent, or Firm* — Merchant & Gould P.C.

(57) ABSTRACT

A linear proton accelerator includes a plurality of accelerator components arranged after one another, and a proton source and a plurality of accelerating units. The accelerator further includes a reticular support structure for supporting the accelerator components. The support structure is shaped as a prism with a polygonal cross-section, and has a plurality of side faces joining opposite ends of the prism. The support structure is arranged concentrically with respect to the accelerator components.

9 Claims, 2 Drawing Sheets

SELF-SHIELDED VERTICAL PROTON-LINEAR ACCELERATOR FOR PROTON-THERAPY

BACKGROUND OF THE INVENTION

The present invention is related to an apparatus for the linear acceleration of protons for proton-therapy.

Proton-therapy is a type of particle therapy which uses a beam of protons to irradiate diseased tissue, most often in the treatment of cancer. The main advantage of proton therapy is the ability to more precisely localize the radiation dosage when compared with other types of external beam radiotherapy.

In the past and present, several technical approaches have been pursued for the accelerator that produces the proton beam. Mainly circular accelerators, like cyclotrons (or synchrocyclotrons) and synchrotrons have been used.

Also different types of accelerators have been proposed like linear accelerators, and they are currently under development at some research centers (Italy, CERN).

One of the main problems against the diffusion of proton-therapy is related to the cost of the facility. Despite the undoubtedly superior quality of the proton treatment vs the X-rays radiotherapy, the difference in costs between a proton-therapy installation and the best X-rays installation is still too high to permit a wide diffusion of the proton-therapy treatment.

The cost of a proton-therapy installation is strictly related to the facility layout. The accelerator cost covers only a small portion (usually around 20-30%) of the general cost, the main part being due to infrastructures, building, shielding and electricity.

The major drawback of the circular accelerators for their use in proton-therapy facilities is due just to the plant layout required, and especially to the heavy shielding required by the operation of those accelerators. These accelerators usually lose high energy particles that generate stray radiation to the environment (neutrons and X-rays).

In cyclotrons and synchrocyclotrons a particle is accelerated in circles to the desired energy and then ejected out of the machine by an extraction process whose efficiency is not larger than 70%. So some high energy beam is left inside the accelerator. Circular accelerators are very heavy machines, with weights of the order of 200 to 500 tons and with diameter range from 2 to 6 meters depending if built with superconducting coils or normally conducting coils. The beam energy is fixed to the maximum allowable energy so that to irradiate patients with a lower energy an external degrader has to be used. This, at the same time degrades also the beam quality, in such a way that an emittance filter is needed that transmits only 70%-10% of the generated current, depending on the energy degradation parameters.

In contrast to circular accelerators, linear accelerators known also as "linac" do not circulate the particle, but the particles go through a series of resonant cavities disposed linearly.

A linear accelerator is composed of two essential elements: the resonator, having a function of accelerating the particles; and the focusing system which is used to contain and confine the particle beam.

The main advantages of a linac for the application in proton-therapy consist in the accelerator dimension which is rather small in the transverse dimensions while it expands in the longitudinal dimension.

Moreover in a linac the particle transmission from the lowest to the highest energy can be virtually without particle losses. These two features combine fruitfully so to have an accelerator that can be easily shielded simplifying radio-protection requirements.

U.S. Pat. No. 4,392,080 discloses a linear particle accelerator.

SUMMARY OF THE INVENTION

An object of the present invention is to provide a proton linear accelerator which can be installed in areas with limited spaces.

Accordingly, the invention proposes a linear proton accelerator including a plurality of accelerator components arranged after one another, said accelerator components comprising a proton source and a plurality of accelerating units, said accelerator further including a reticular support structure for supporting said accelerator components, said support structure being shaped as a prism with a polygonal cross-section and having a plurality of side faces joining opposite ends of the prism, wherein said support structure is arranged concentrically with respect to said accelerator components, and wherein a plurality of shielding slabs of radiation shielding material are mounted on respective openings formed on said side faces of the support structure.

The support structure of the present invention allows the linac to be positioned in any direction, even vertically, being the structures light and easily mountable. Therefore a vertical linac can be envisaged. Such a linac can be positioned in a tower with only the treatment room well sited in the basement of an existing hospital facility. This arrangement, not possible with any other type of accelerator, if not a linac, can solve installation problems in areas with limited space.

BRIEF DESCRIPTION OF THE DRAWINGS

A preferred, but non-limiting, embodiment of the invention will now be described, with reference to the attached drawings, in which.

DETAILED DESCRIPTION

Figure 1:
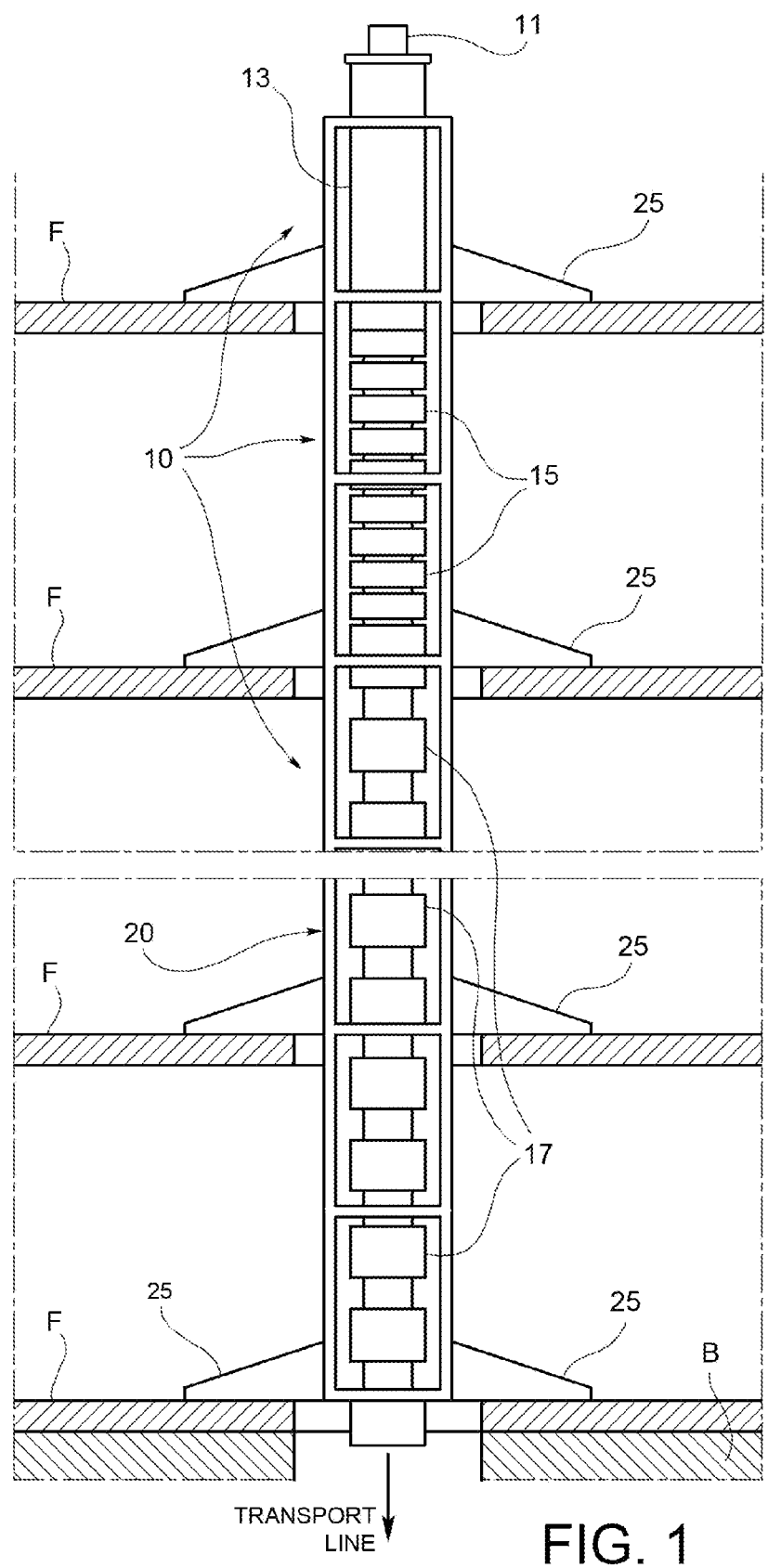
FIG. 1 is a schematic, elevation side view showing a proton linear accelerator according to the invention.

With reference to FIG. 1, a linear accelerator according to a preferred embodiment of the invention is shown. This accelerator comprises conventionally a plurality of accelerator components 10 arranged after one another, and rigidly connected to one another so as to form a single string structure. Particularly, said accelerator components comprise a proton source 11, preferably a duoplasmatron or microwave proton source that delivers a pulsed proton beam up to 40 keV, an injector 13, preferably a radio-frequency quadrupole (RFQ) injector working in the RF frequency range between 350 MHz and 750 MHz that increases the energy of the proton beam in the range 3-5 MeV, and a plurality of accelerating units 15, 17, preferably a 3 GHz side coupled drift tube linac (SCDTL) segment composed by several SCDTL units 15, increasing the energy of the proton beam up to an energy in the range 30-70 MeV, followed by a 3 GHz coupled cavity linac (CCL) segment composed by several CCL units, increasing the energy of the proton beam up to 230-250 MeV.

In the SCDTL units 15 the focusing would come from having short tanks composed of a few cells each and a quadrupole focusing between tanks.

in the CCL in order to focus the beam, cells are put together into tanks of limited length (a tank contains usually between 14 and 20 accelerating cells) and between the tanks permanent quadrupoles (PMQ) are placed; the electromagnetic field passes from one tank to the next via a bridge coupler.

The power for the full linac will be provided by several RF power units (not shown). Every power unit will be composed by a modulator and a klystron. The power is delivered to the accelerating tanks via the RF network system.

Figure 2:
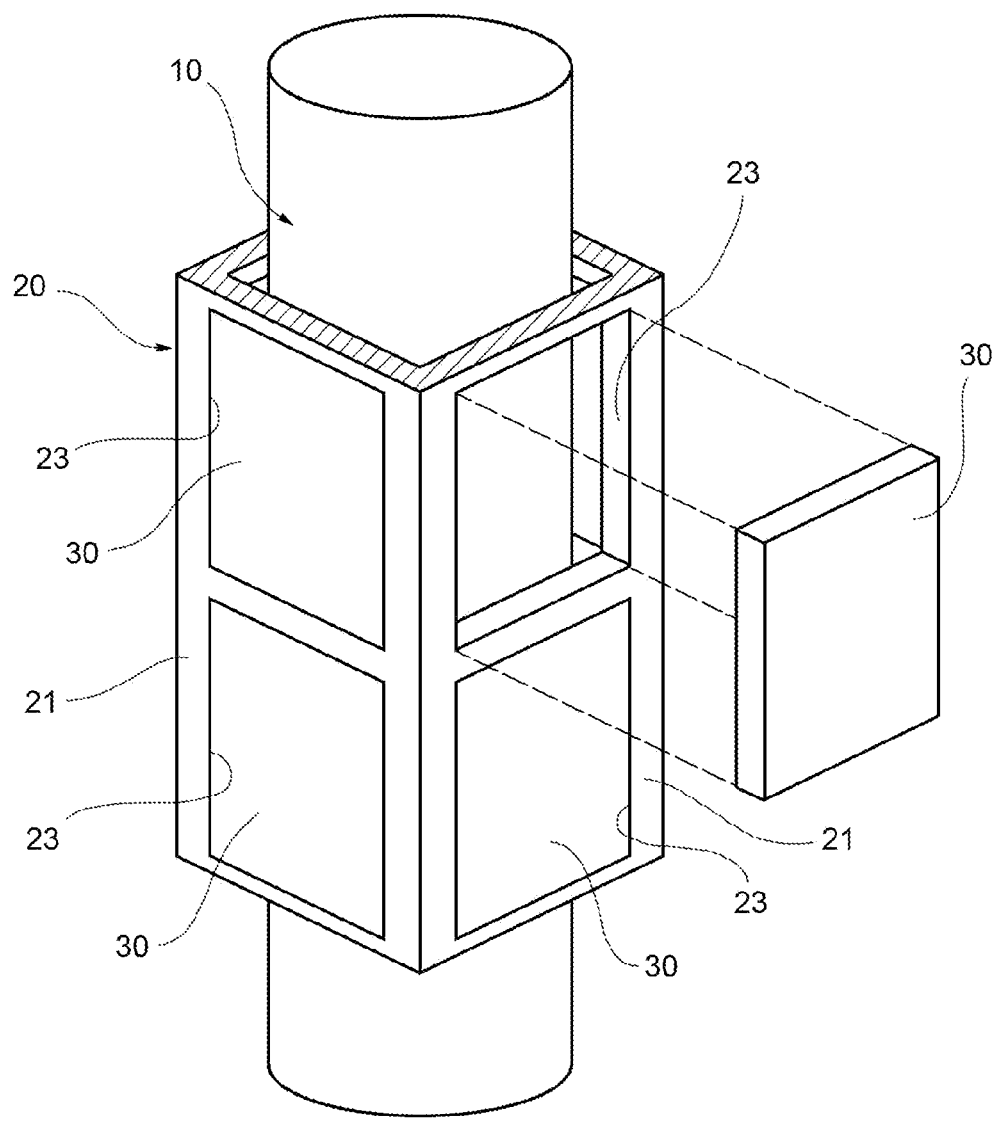
FIG. 2 is a schematic, perspective view of a segment of the accelerator of FIG. 1.

The proton linear accelerator according to the invention further includes a reticular support structure 20 for supporting the accelerator components 10. As clearly shown in FIG. 2, the support structure 20 is shaped as a prism with a polygonal, particularly square, cross-section, and having a plurality of side faces 21 joining opposite ends of the prism. From a structural point of view, the support structure 20 is composed of a network of beams interconnected so as to form a prism-shaped framework. Such an arrangement of beams defines a plurality of openings 23 on the side faces 21 of the prism. In the embodiment shown in the drawings, these openings are configured as square-shaped windows.

The support structure 20 is arranged concentrically with respect to the accelerator components 10. Connection means (not shown) are provided between at least some of the accelerator components 10 and the support structure 20, for connecting the linear accelerator to the support structure 20 and enabling the linear accelerator to be supported by the support structure 20.

In particular, the linear accelerator and the support structure 20 are positioned vertically. For example, they may be installed within a shaft formed in a multi-floor building such as a tower. To this end, the support structure 20 is equipped with a plurality of side brackets 25 extending laterally from and integral with the support structure 20; by means of the side brackets 25 the support structure 20 rests on several floors F of the multi-floor building.

Treatment rooms (not show) are formed within a basement B of the building; a beam transport line composed of magnetic dipoles and quadrupoles is provided at the output (lower) end of the linear accelerator for delivering the proton beam to the treatment rooms.

The self-shielded compact proton linear accelerator for proton-therapy in the preferred embodiment is equipped with a local radiation shield, that prevents the outflow of the spurious radiation (neutrons, gamma rays) generated in the structure by the very few beam losses.

The local radiation shield (shown in FIG. 2) are slabs 30 of radiation shielding material mounted on the openings 23 formed on the side faces 21 of the support structure 20. Radiation shielding material is preferably selected from the group consisting of hydrogenated material, cadmium, lead or any combination of these. The shielding slabs 30 are positioned very close the accelerator components 10 and are mounted on the framework 20.

What is claimed is:

1. A linear proton accelerator including a plurality of accelerator components arranged after one another, said accelerator components comprising:
    a proton source;
    a plurality of accelerating units; and
    a reticular support structure for supporting said accelerator components, said support structure being shaped as a prism with a polygonal cross-section, and having a plurality of side faces joining opposite ends of the prism, wherein said support structure is arranged concentrically with respect to said accelerator components;
    wherein a plurality of shielding slabs of radiation shielding material are mounted on respective openings formed on said side faces of the support structure; and
    wherein the support structure further comprises a plurality of side brackets extending laterally with the support structure extending vertically with the side brackets configured to engage a plurality of floors of a multi-floor building.

2. An accelerator according to claim 1, wherein said proton source is a duoplasmatron or microwave proton source.

3. An accelerator according to claim 1, wherein said accelerator components further comprise an injector arranged after the proton source.

4. An accelerator according to claim 3, wherein said injector comprises a radio-frequency quadrupole injector arranged after the proton source.

5. An accelerator according to claim 1, wherein said accelerating units comprise a plurality of side coupled drift tube linac units and a plurality of coupled cavity linac units.

6. An accelerator according to claim 1, wherein said accelerator and support structure are positioned vertically.

7. An accelerator according to claim 6, wherein said support structure is configured for being installed within a multi-floor building, and is equipped with a plurality of side brackets extending laterally from the support structure, said side brackets being provided for supporting the support structure on respective floors of the multi-floor building.

8. A linear proton accelerator including a plurality of accelerator components arranged after one another, said accelerator components comprising:
    a proton source;
    a plurality of accelerating units;
    a reticular support structure for supporting said accelerator components;
    means for connecting for connecting at least some of the accelerating units and the reticular support structure; and
    wherein said support structure is shaped as a prism with a polygonal cross-section, and having a plurality of side faces joining opposite ends of the prism, wherein said support structure is arranged concentrically with respect to said accelerator components;
    wherein a plurality of shielding slabs of radiation shielding material are mounted on respective openings formed on said side faces of the support structure.

9. A linear proton accelerator including a plurality of accelerator components arranged after one another and connected to one another to form a string structure, said accelerator components comprising:
    a proton source;
    a plurality of accelerating units; and
    a reticular support structure for supporting said accelerator components, said support structure comprising a network of interconnected beams, said network of interconnected beams forming a prism-shaped framework with a polygonal cross-section, and having a plurality of side faces joining opposite ends of the prism-shaped network, wherein said support structure is arranged concentrically with respect to said string structure;
    wherein a plurality of shielding slabs of radiation shielding material are mounted on respective openings formed on said side faces of the support structure and defined by the network of interconnected beams.

* * * * *